United States Patent
Reuter et al.

(10) Patent No.: US 12,338,366 B2
(45) Date of Patent: Jun. 24, 2025

(54) USE OF RHAMNOLIPIDS AND/OR SOPHOROLIPIDS IN COATING COMPOSITIONS FOR OBTAINING A HOMOGENEOUS COLOUR APPEARANCE OF THE DRY COATING FILM AND/OR FOR INCREASING OCCUPATIONAL SAFETY IN THE PRODUCTION OF COATING COMPOSITIONS

(71) Applicant: Evonik Operations GmbH, Essen (DE)

(72) Inventors: Ellen Reuter, Bochum (DE); Stefan Silber, Krefeld (DE); Petra Allef, Essen (DE); Katrin Roland, Essen (DE); Pedro Cavaleiro, Cologne (DE); Jochen Mergenthaler, Essen (DE); Claudia Jansen, Leverkusen (DE); Marco Blei, Essen (DE)

(73) Assignee: Evonik Operations GmbH, Essen (DE)

( * ) Notice: Subject to any disclaimer, the term of this patent is extended or adjusted under 35 U.S.C. 154(b) by 355 days.

(21) Appl. No.: 17/547,575

(22) Filed: Dec. 10, 2021

(65) Prior Publication Data
US 2022/0186048 A1    Jun. 16, 2022

(30) Foreign Application Priority Data
Dec. 15, 2020   (EP) .................... 20214083

(51) Int. Cl.
*C09D 7/63*   (2018.01)
*C07H 15/06*   (2006.01)
*C09D 7/41*   (2018.01)

(52) U.S. Cl.
CPC ............. *C09D 7/63* (2018.01); *C07H 15/06* (2013.01); *C09D 7/41* (2018.01)

(58) Field of Classification Search
CPC . C09D 7/63; C09D 7/41; C09D 5/027; C09D 5/028; C09D 17/001; C09D 17/003;
(Continued)

(56) References Cited

U.S. PATENT DOCUMENTS

| 5,629,367 A | * | 5/1997 | Lofftus | G03G 9/0804 |
| | | | | 523/333 |
| 7,811,378 B2 | * | 10/2010 | Nungeβ | C09B 67/0097 |
| | | | | 106/447 |

(Continued)

FOREIGN PATENT DOCUMENTS

| CN | 104263103 A | * 1/2015 | ........... C09D 125/14 |
| CN | 105602367 | 5/2016 | |

(Continued)

OTHER PUBLICATIONS

Platinum Painting Keller: How is Paint Made? [online; Feb. 5, 2020]. Retrieved from the Internet < URL: https:// www.platinumpaintingkeller.com/blog/2020/02/05/how-is-paint-made/> (Year: 2020).*

(Continued)

*Primary Examiner* — Colin W. Slifka
(74) *Attorney, Agent, or Firm* — Grüneberg and Myers PLLC

(57) ABSTRACT

Rhamnolipids and/or sophorolipids can be used in coating compositions for improvement of the speed of wetting of pulverulent formulation constituents in such compositions, which leads to a reduction in dust nuisance during incorporation thereof and to the increase in occupational safety in the production of coating compositions. Rhamnolipids and/or sophorolipids can also be used in coating compositions for obtaining improved homogeneous colour appearance of the dry paint film with regard to difference in hue, ascertained from the delta E and visual assessment.

18 Claims, 2 Drawing Sheets

(58) Field of Classification Search
CPC ...... C09D 17/005; C09D 17/007; C09D 7/45; C09D 193/00; C09D 11/08; C07H 15/06; C08K 5/1545; C08K 5/159
USPC ...................................................... 106/162.1
See application file for complete search history.

(56) References Cited

U.S. PATENT DOCUMENTS

| | | | |
|---|---|---|---|
| 2011/0237531 A1* | 9/2011 | Yanagisawa | A61K 8/60 252/182.28 |
| 2013/0296461 A1 | 11/2013 | Sadasivan | |
| 2020/0140694 A1 | 5/2020 | Gage et al. | |
| 2021/0277257 A1 | 9/2021 | Roland et al. | |
| 2022/0041887 A1 | 2/2022 | Roland et al. | |
| 2022/0082484 A1 | 3/2022 | Isken et al. | |
| 2022/0082508 A1 | 3/2022 | Isken et al. | |
| 2022/0084181 A1 | 3/2022 | Isken et al. | |
| 2022/0186075 A1 | 6/2022 | Reuter et al. | |

FOREIGN PATENT DOCUMENTS

| | | | |
|---|---|---|---|
| EP | 1889623 | 2/2008 | |
| EP | 2847285 | 7/2016 | |
| EP | 3006505 | 7/2017 | |
| WO | 01/10447 | 2/2001 | |
| WO | 2014/027249 | 2/2014 | |
| WO | WO-2016053577 A1 * | 4/2016 | ............ A01N 25/10 |
| WO | 2018/220577 | 12/2018 | |

OTHER PUBLICATIONS

Machine translation of CN-104263103-A originally published Jan. 2015 to Chen (Year: 2015).*

Kotake et al., Influence of dry and wet grinding conditions on fineness and shape of particle size distribution of product in a ball mill, available online 2010, Advanced Powder Technology 22 (2011) 86-92 (Year: 2010).*

Hosokawa Alpine Group: Ball Mills and Agitated Media Mills Grinding wet and dry [online], [retrieved on Dec. 19, 2024]. Retrieved from the internet: < URL: https://www.hosokawa-alpine.com/powder-particle-processing/machines/ball-mills-agitated-media-mills/> (Year: 2024).*

Abdel-Mawgoud et al., "Rhamnolipids: diversity of structures, microbial origins and roles", Appl. Microbiol Biothechnol, vol. 86, 2010, pp. 1323-1336.

European Search Report issued Jul. 6, 2021 in European Application No. 20214083.6, pages.

Howe et al., "Biophysical characterization of synthetic rhamnolipids", The FEBS Journal, vol. 273, 2006, pp. 5101-5112.

Miao et al., "Ethylation of Di-rhamnolipids: A Green Route to Produce Novel Sugar Fatty Acid Nonionic Surfactants", J. Surfact Deterg, vol. 17, 2014, pp. 1069-1080.

U.S. Appl. No. 17/190,919, filed Mar. 3, 2021, 2021/0277257, Roland et al.

U.S. Appl. No. 17/643,630, filed Dec. 10, 2021, 2022/0186075, Roland et al.

U.S. Appl. No. 17/395,616, filed Aug. 6, 2021, 2022/0041887, Roland et al.

U.S. Appl. No. 17/476,785, filed Sep. 16, 2021, 2022/0082484, Isken et al.

U.S. Appl. No. 17/477,025, filed Sep. 16, 2021, 2022/0084181, Isken et al.

U.S. Appl. No. 17/476,983, filed Sep. 16, 2021, 2022/0082508, Isken et al.

European Search Report dated Mar. 21, 2022 in European Application No. 21213139.5, 5 pages.

* cited by examiner

USE OF RHAMNOLIPIDS AND/OR SOPHOROLIPIDS IN COATING COMPOSITIONS FOR OBTAINING A HOMOGENEOUS COLOUR APPEARANCE OF THE DRY COATING FILM AND/OR FOR INCREASING OCCUPATIONAL SAFETY IN THE PRODUCTION OF COATING COMPOSITIONS

CROSS-REFERENCE TO RELATED APPLICATIONS

This application claims priority to European Patent Application No. 20214083.6, filed on Dec. 15, 2020, the content of which is hereby incorporated by reference in its entirety.

BACKGROUND OF THE INVENTION

Field of the Invention

The invention relates to the use of rhamnolipids and/or sophorolipids in coating compositions for obtaining a homogeneous colour appearance of the dry coating film and/or for increasing occupational safety in the production of coating compositions.

Description of Related Art

Coatings are applied to surfaces for decorative and/or for protective purposes. Formulations used for many coating tasks contain particles such as pigments and/or fillers.

Pigments are colouring substances present in insoluble dispersed form in the application medium. Application media are, for example, paints, coating materials, pigment preparations, printing inks or else organic solvents and other formulations in which the pigment is incorporated. Typically, the crude pigments formed in the synthesis are employed in ground or comminuted form; for example, what are called dry grinding and wet grinding methods are used. However, particles of small diameter have a particularly high tendency to agglomerate and therefore have to be stabilized.

The stabilization of the pigments is of great significance in the coatings industry, since pigments, being an important formulation constituent, determine the visual appearance and the physicochemical properties of a coating. In order that they can display their action to an optimal degree in the coating, they have to be homogeneously and finely distributed in the varnish during the dispersion process. The distribution has to be stabilized, in order that this state is maintained in the course of production, storage, processing and subsequent film formation. Recombination of the primary particles and aggregates can lead, for example, to inadequate colour depth, floating of the pigments and/or poor reproducibility of colour shades.

Commercial paint formulations are mono-pigmented only some cases; frequently, mixtures of two or more different pigments will be involved. In such systems too, all pigments should be well-wetted and as far as possible be deflocculated and distributed homogeneously throughout the paint film. But if this mixture is disrupted because the pigments separate, this results in changes in hue in the paint. This defect is designated as "floating".

One of the causes of the separation of the pigments is flow phenomena in the drying paint film. During the phase of drying of a paint film, solvent has to be transported out of the lower paint layers to the surface; in the course of evaporation, there is an increase in the density of the remaining material, resulting in settling. In addition, in the course of evaporation, cooling effects occur and the surface tension changes. All this leads to formation of vortex currents that can be manifested in the form of more or less uniform hexagonal cells (called Bénard cells). The paint material rises upward in the centre of the cells, then is distributed across the surface and flows back downward at the cell boundaries. These cell flows have long been known—not just in paint. In a pigmented system, pigments are also involved in these vortex flows and, assuming that the mobility of the different pigments is similar, they are also transported in a very similar manner in the vortices and there is no separation. But if there is a distinct difference in the pigment mobilities, the transport characteristics are also different and there can be separation.

This effect causes the dry coating film to have a spotty appearance, for example.

The rub-out test, including determination of the difference in hue (delta E), of the rubbed from the unrubbed surface is a standard method of testing these floating effects or else flocculation effects; this is described, for example, in Groteklaes M, Rub-out-Effekt, RD-18-01991 (2005) in Böckler F., Dill B., Eisenbrand G., Faupel F., Fugmann B., Gamse T., Matissek R., Pohnert G., Rühling A., Schmidt S., Sprenger G., RÖMPP [Online], Stuttgart, Georg Thieme Verlag, [Nov. 2021] roempp.thieme.de/lexicon/RD-18-01991. These effects have an adverse effect on the homogeneous colour appearance of the dry paint film. In addition, these unwanted effects in the dried paint films are frequently assessed visually under standard light conditions.

Application media, coating systems, coating compositions, paint formulations and paint media are used as synonyms in the context of the present invention.

The prior art discloses, for example, polymeric wetting agents and dispersants which firstly contain groups having pigment affinity, such as carboxyl, amino or phenyl functionalities, and secondly contain side chains soluble in the medium. The groups having pigment affinity are ideally to have a rapid orientation to the surface of pigments and a high permanence thereon. Side chains ensure the compatibility with the dispersion medium or paint medium and steric stabilization of the dispersed phase.

Some publications also mention biosurfactants as dispersant, as defoamer, as wetting agent or as emulsifier in paints and coating materials. Known representatives of these biosurfactants are rhamnolipids and sophorolipids. These lipids are nowadays produced with wild-type isolates of various yeasts, especially with *Candida bombicola*.

EP 3 006 505 describes, for example, a coating composition comprising a dispersion consisting of a binder, a biocide and a biosurfactant consisting of rhamnolipids and sophorolipids. EP 2 847 285 discloses a similar composition, wherein the isothiazolone biocide is specifically added. Both documents disclose the synergistic biocide action of the rhamnolipids and sophorolipids with a biocide.

In the incorporation of the finely ground particles into the application medium, there can be dust pollution in the production hall. In this operating step, as is well known, employees, for example, open the sacks containing the particles and pour the contents into an open vessel that has been initially charged with the application medium. In large-scale production plants, the particles stored in silos are added to the application medium. Subsequently, the stirring-in operation is commenced. It is also known that the stirring-in operation can be conducted during the addition of the particles. This throws up a lot of dust for as long as pigments are in powder form on the surface of the liquid application medium. Fine particles can penetrate into the fine alveoli of the lung, where they can cause diseases, Many companies have therefore installed suction hood devices in order to minimize exposure of employees to dust. In addition, employees frequently have to wear respiratory masks, which means high buildup of heat under the respiratory equipment.

SUMMARY OF THE INVENTION

It would therefore be desirable to identify substances that reduce dust pollution in the production of coating compositions. It would also be desirable to use substances in coating compositions in order to achieve a homogeneous colour appearance of the dry coating films without impairing other properties, for example hue or colour locus.

It has now been found that, surprisingly, the use of rhamnolipids and/or sophorolipids in coating compositions is suitable for improvement of the speed of wetting of pulverulent formulation constituents in such compositions, which leads to a reduction in dust nuisance during incorporation thereof and hence to the increase in occupational safety in the production of coating compositions, with assurance or improvement of the retention of a homogeneous colour appearance of the dry coating film.

It has possibly additionally been found that the dry coating film, through the use of rhamnolipids and/or sophorolipids, has an improved homogenous colour appearance with regard to difference in hue, ascertained from the delta E, and visual assessment, as described below, compared to a conventional coating film without rhamnolipids and/or sophorolipids.

A further advantage is the shortening of the time taken to introduce the particles into the application medium, which means optimization of the process duration.

Pulverulent formulation constituents, solids, pigments and particles are used as synonyms.

The invention also includes the following embodiments:
1. Use of rhamnolipids and/or sophorolipids in coating compositions for improvement of the speed of wetting of pulverulent formulation constituents in such compositions, which leads to a reduction in dust nuisance during incorporation thereof, and hence to the increase in occupational safety in the production of coating compositions and to the obtaining of improved homogeneous colour appearance of the dry paint film with regard to difference in hue, ascertained from the delta E, and visual assessment.
2. Use according to embodiment 1, characterized in that the coating compositions are paints and coating materials selected from interior wall paints, exterior paints, architectural paints, floor coatings, wood paints, industrial paints, automotive OEM or refinishing paints, primers, primer-surfacers, basecoats and topcoats.
3. Use according to embodiment 1, characterized in that the use takes place in pigment concentrates, colour pastes, pigment pastes or millbases.
4. Use according to any of the preceding embodiments, characterized in that the coating compositions include solids selected from fillers, pigments, dyes, optical brighteners, ceramic materials, magnetic materials.
5. Use according to any of the preceding embodiments, characterized in that the coating compositions comprise further additives, preferably wetting agents, dispersing additives, rheology additives, levelling aids or defoamers.
6. Use according to any of the preceding embodiments, characterized in that the rhamnolipids are compounds of the general formula (I) or a salt thereof

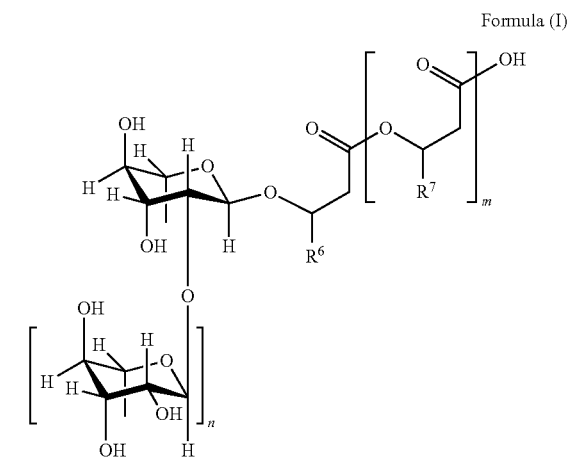

Formula (I)

where $m=2$, 1 or 0, especially 1 or 0, $n=1$ or 0, especially 1, $R^8$ and $R^7$=independently an identical or different organic radical having 2 to 24, preferably 5 to 13, carbon atoms, especially optionally branched, optionally substituted, especially hydroxy-substituted, optionally unsaturated, especially optionally mono-, di- or triunsaturated, alkyl radical, preferably those selected from the group consisting of pentenyl, heptenyl, nonenyl, undecenyl and tridecenyl and $(CH_2)_x$—$CH_3$ with $x=1$ to 23, preferably 4 to 12.

7. Use according to any of the preceding embodiments, characterized in that the rhamnolipids are a mixed composition with >90% diRL.
8. Use according to any of the preceding embodiments, characterized in that the rhamnolipids are a mixed composition comprising rhamnolipids, characterized in that the mixed composition contains 51% by weight to 95% by weight of diRL-C10C10 and 0.5% by weight to 9% by weight of monoRL-C10C10, where the percentages by weight are based on the sum total of all rhamnolipids present, with the proviso that the weight ratio of di-rhamnolipids to mono-rhamnolipids is greater than 91:9, preferably greater than 97:3, more preferably greater than 98:2.

9. Use according to any of the preceding embodiments, characterized in that the rhamnolipids are a mixed composition comprising rhamnolipids, characterized in that the mixed composition contains 0.5% by weight to 15% by weight of diRL-C10C12:1, where the percentages by weight are based on the sum total of all rhamnolipids present.
10. Use according to any of the preceding embodiments, characterized in that the sophorolipids are compounds of the formula (II) or (IIa)

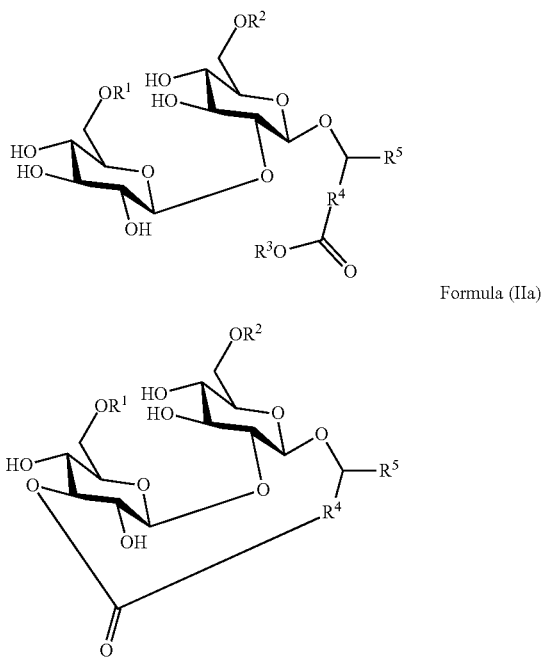

Formula (II)

Formula (IIa)

where
R$^1$ and R$^2$ are independently either H or an acetyl group,
R$^3$ is H, a methyl, ethyl or hexyl group,
R$^4$ is independently a saturated or unsaturated divalent branched or unbranched organic group,
R$^5$ is H or a methyl group,
with the proviso that the total number of the carbon atoms in the groups R$^4$ and R$^5$ do not exceed the number 29.

11. Use according to any of the preceding embodiments, characterized in that rhamnolipids and/or sophorolipids are used within a range from 0.01% by weight to 10.0% by weight, more preferably 0.1% by weight to 5.0% by weight, based on the overall coating composition.

DETAILED DESCRIPTION OF THE INVENTION

Figure 1:
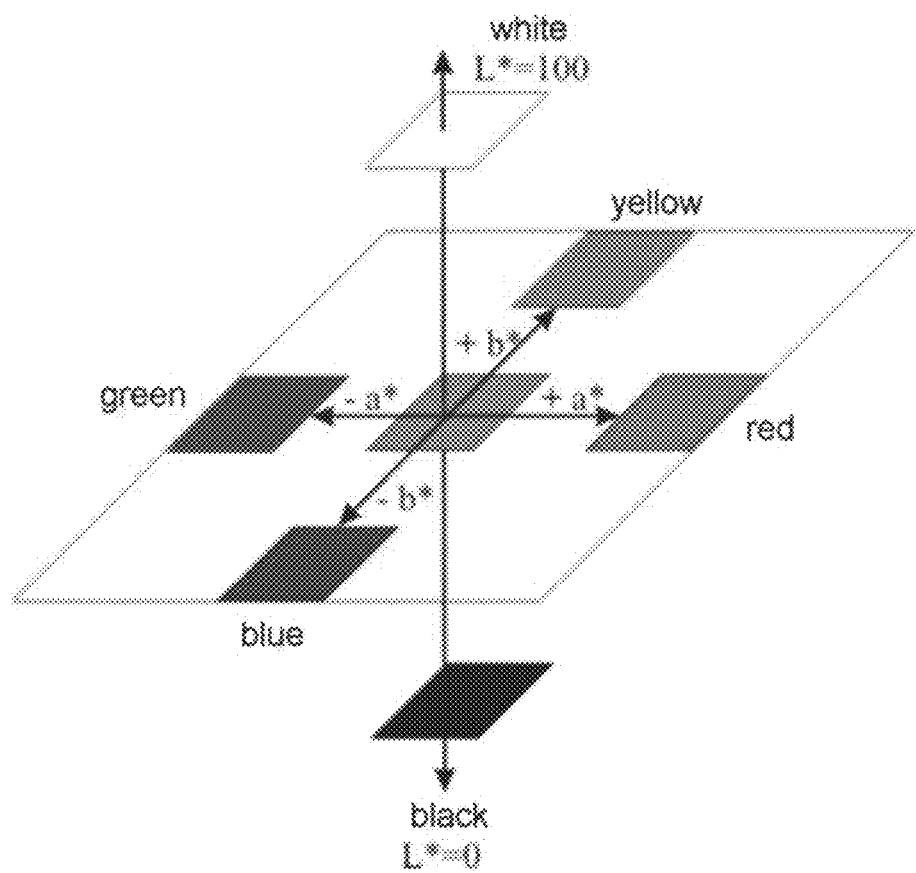
FIG. 1 shows a diagram of a colour model with colour loci based on a coordinate system.

The coating compositions are preferably preparations for various fields of application that are applied to the substrate to be coated by application methods such as, for example, spraying, dipping, rolling or painting application, and various printing methods.

Examples of coating materials in the context of the present invention are paints, coating materials, printing inks and other coating materials, such as solventborne or aqueous coatings and solvent-free coatings, powder coatings, UV-curable coatings, low-solids, medium-solids and high-solids, automotive coatings, wood coatings, baked coatings, 2-component coatings, metal coating materials, toner compositions. Further examples of coating materials are given in "Bodo Müller, Ulrich Poth, Lackformulierung und Lackrezeptur, Lehrbuch für Ausbildung und Praxis [Coating Formulation and Coating Composition, Textbook for Training and Practice], Vincentz Verlag, Hanover (2003), 73-1996" and "P. G. Garrat, Strahlenhärtung [Radiative Curing], Vincent Verlag, Hanover (1996)".

The paints and coating materials are interior wall paints, exterior paints, architectural paints, floor coatings, wood paints, industrial paints, paints for automotive OEM (original equipment manufacturer) or refinishing, primers, primer-services, basecoats and topcoats.

Examples of printing inks and/or printing varnishes in the context of the present invention are solvent-based or aqueous printing inks, flexographic printing inks, intaglio printing inks, letterpress or relief printing inks, offset printing inks, lithographic printing inks, printing inks for printing of packaging, screenprinting inks, printing inks such as printing inks for inkjet printers, inkjet ink, printing varnishes such as overprint varnishes. Further printing ink and/or printing varnish formulations are given in "E. W. Flick, Printing Ink and Overprint Varnish Formulations—Recent Developments, Noyes Publications, Park Ridge, N.J., (1990)" and subsequent editions.

The coating compositions preferably include solids selected from the group of the fillers, pigments, dyes, optical brighteners, ceramic materials, magnetic materials.

Examples of pigments are those from the group of inorganic pigments, such as carbon blacks, titanium dioxides, zinc oxides. Prussian blue, iron oxides, cadmium sulfides, chromium pigments, for example chromates, molybdates and mixed chromates and sulfates of lead, zinc, barium, calcium and mixtures thereof. Further examples of inorganic pigments are specified in the book "H. Endriss, Aktuelle anorganische Bunt-Pigmente [Inorganic Colour Pigments Today], Vincentz Verlag, Hannover (1997)".

Examples of organic pigments are those from the group of the azo, diazo, condensed azo, naphthol, metal complex, thioindigo, indanthrone, isoindanthrone, anthanthrone, anthraquinone, isodibenzanthrone, triphendioxazine, quinacridone, perylene, diketopyrrolopyrrole and phthalocyanine pigments. Further examples of organic pigments are specified in the book "W. Herbst, K. Hunger, Industrial Organic Pigments, VCH, Weinheim (1993)".

Examples of fillers are those from the groups of talc, kaolin, silicas, barytes and lime; ceramic materials, for example aluminium oxides, silicates, zirconium oxides, titanium oxides, boron nitrides, silicon nitrides, boron carbides, mixed silicon aluminium nitrides and metal titanates; magnetic materials, for example magnetic oxides of transition metals, such as iron oxides, cobalt-doped iron oxides and ferrites; metals, for example iron, nickel, cobalt and alloys thereof.

The person skilled in the art will be aware that such coating compositions may include further ingredients. As liquid medium, they may contain organic solvents (e.g. acetates such as butyl or ethyl acetate, hydrocarbons such as petroleum spirits of various boiling ranges, alcohols, ethers, glycols and glycol ethers) and/or water, as known as prior art depending on the binders used.

It is possible to use customary binders. It is possible with preference to use alkyd, acrylate, styrene-acrylate, epoxy, polyvinylacetate, polyester or polyurethane binders. Any kind of curing is possible, for example by oxidative drying, physical drying, self-crosslinking, UV or electron beam curing or crosslinking by baking.

It is conceivable that the coating composition comprises further additives, for example preferably wetting agents, dispersing additives, rheology additives, levelling aids or defoamers.

The person skilled in the art is aware that the production of coating compositions comprising particles can be effected, for example, by the use of pigment concentrates, colour paste, pigment pastes or liquid formulations of the particles. However, it is also possible to produce a millbase in order to use it in a timely manner for the production of coating compositions.

The invention therefore preferably also provides for use of rhamnolipids and/or sophorolipids in pigment concentrates, colour paste, pigment paste or liquid formulations of the particles or millbases.

Rhamnolipids and sophorolipids are surfactants which can be prepared by means of fermentation.

Rhamnolipids are composed of one to two rhamnose units and one to three, mostly β-hydroxy fatty acids. The fatty acids can be saturated or unsaturated.

The variation in the chain length and number (congener) of the fatty acid portions has been described in a number of publications (Howe et al., FEBS J. 2006; 273(22):5101-12; Abdel-Mawgoud et al., Appl Microbiol Biotechnol, 86, 2010; p. 1323-1336).

Miao et al., Journal of Surfactants and Detergents, 17 (6), 2014; 1069-1080, describes the synthesis of di-rhamnolipid ethyl esters by esterification with ethanol and also the suitability of the esters as nonionic surfactant.

WO2001010447 and EP1889623 disclose the pharmaceutical and cosmetic applications of rhamnolipids and short-chain rhamnolipid esters (C1-C6; methyl to hexyl esters, linear or branched), in particular in wound healing.

The rhamnolipids are preferably compounds of the general formula (I) or salts thereof

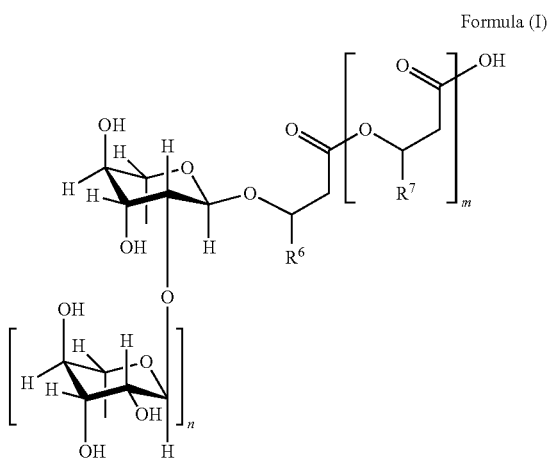

Formula (I)

where
m=2. 1 or 0, in particular 1 or 0,
n=1 or 0, in particular 1,
$R^6$ and $R^7$=independently an identical or different organic radical having 2 to 24, preferably 5 to 13, carbon atoms, especially optionally branched, optionally substituted, especially hydroxy-substituted, optionally unsaturated, especially optionally mono-, di- or triunsaturated, alkyl radical, preferably those selected from the group consisting of pentenyl, heptenyl, nonenyl, undecenyl and tridecenyl and $(CH_2)_x$—$CH_3$ with x=1 to 23, preferably 4 to 12.

Preference is given to a mixed composition of rhamnolipids containing >90% diRL.

Preference is given to a mixed composition of rhamnolipids containing
51% by weight to 95% by weight of diRL-C10C10 and
0.5% by weight to 9% by weight of monoRL-C10C10, where the percentages by weight are based on the sum total of all rhamnolipids present, with the proviso that the weight ratio of di-rhamnolipids to mono-rhamnolipids is greater than 91:9, preferably greater than 97:3, more preferably greater than 98:2.

For the use according to the invention, preference is given to using a rhamnolipid mixture containing 0.5% by weight to 15% by weight of diRL-C10C12:1, where the percentages by weight are based on the sum total of all rhamnolipids present.

The sophorolipids are preferably compounds of the formula (II) or (IIa)

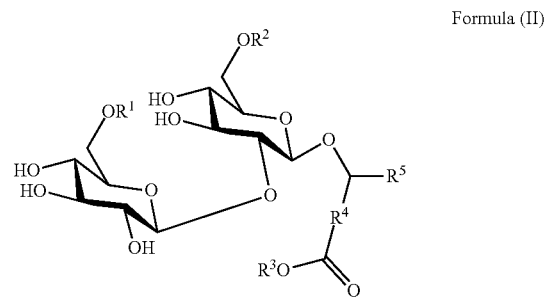

Formula (II)

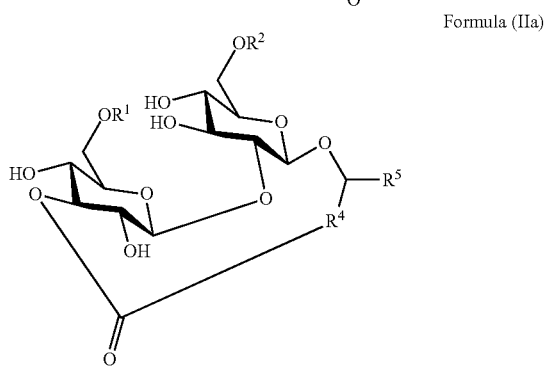

Formula (IIa)

where
$R^1$ and $R^2$ are independently either H or an acetyl group,
$R^3$ is H, a methyl, ethyl or hexyl group,
$R^4$ is independently a saturated or unsaturated divalent branched or unbranched organic group,
$R^5$ is H or a methyl group,
with the proviso that the total number of the carbon atoms in the groups $R^4$ and $R^5$ do not exceed the number 29.

Rhamnolipids are available under the Natsurfact name from Stepan (Northfield, Ill., USA) and RHEANCE® One from Evonik Operations GmbH.

Sophorolipids are available under the HoneySurf name from Holiferm Limited (Manchester, UK) and REWOFERM® SL ONE from Evonik Operations GmbH.

Preference is given to using rhamnolipids and/or sophorolipids within a range from 0.01% by weight to 10.0% by weight, more preferably 0.1% by weight to 5.0% by weight, based on the overall coating composition.

Preference is given to using the rharnnolipids and sophorolipids of the general formulae (I), (II) and (IIa) for accelerating the wetting of pulverulent formulation constituents in coating compositions.

Preference is given to using the rhamnolipids and sophorolipids of the general formulae (I), (II) and (IIa) for optimizing the process regime in the production of coating compositions of pigment concentrates, colour pastes, pigment pastes or millbases.

The invention is to be elucidated in detail hereinafter by working examples.

Methods

Rub-Out Test (Delta E) and Visual Assessment

For the rub-out test, the coating compositions were applied with a 150 μm applicator from Leneta to a test base or test substrate. After the drying time of 5 minutes, the rub-out test was conducted, which involves mixing the paint applied by circular movements with a grinding body, for example a gloved finger, with moderate contact pressure. There should be no occurrence here either of complete pushing of the coating away from the substrate or of tearing of the paint film.

After the paint films have been dried at room temperature for seven days, the colour values are determined in the area where the rub-out test was done and on an adjacent area not subjected to the rub-out test. The two values are used to calculate the ΔE (delta E). This difference in the colour loci is a measurement of the quality of pigment stabilization.

The colour values and the Delta E value were determined with an X-Rite Model SP 62 spectrometer. As is well known, the L*a*b* colour space describes all perceivable colours. It uses a three-dimensional colour space in which the brightness value L* stands vertical on the colour plane (a*, b*). The colour model is standardized in EN ISO 11664-4 "Colorimetry—Part 4: CIE 1976 L*a*b* Colour space". Typically, the measuring instrument measures the values L*, a* and b*. These values then result in a colour locus in a coordinate system, where L* indicates the brightness (0=black; 100 =white), a* the red/green value (−green/+red) and b* the blue/yellow value (−blue/+yellow). (see FIG. 1)

The visual assessment of the dried films with regard to spottiness and the differences in hue of the rubbed area compared to the unrubbed area was made in a colour inspection cabin with D65 daylight illumination using the following assessment scale:
  0=homogeneous, no spots, no differences in colour
  1=very slight spots, very slight differences in hue
  2=slight spots, slight differences in hue
  3=significant spots, significant differences in hue
  4=very significant spots, very significant differences in hue

EXAMPLES

1. Production of the Pigment Concentrates

Pigment concentrates were first produced according to the figures from the respective tables, Tables 1.2-1.4. For production of these pigment concentrates, the liquid constituents were first weighed out and then the pigments were added. After addition of grinding bodies (glass beads of diameter 2-3 mm, same volume as the pigment concentrate), dispersion was effected for one hour (inorganic pigments) or two hours (organic pigments and carbon black) in an agitator (FAS 500 from Lau GmbH) with air cooling. The grinding bodies were sieved off. The resultant filtrate is the pigment concentrate.

The comparative examples were produced analogously with Tego® Dispers 755.

TABLE 1.1

Materials used

| Trade name | Description | Manufacturer |
|---|---|---|
| Water, deionized | | Evonik Operations GmbH |
| Bayferrox 130 M | Pigment | Lanxess AG |
| Heliogen Blue L7101F | Pigment | BASF AG |
| Special Black 4 | Pigment, carbon black | Orion Engineered Carbons GmbH |
| Tego ® Dispers 755 | Copolymer | Evonik Operations GmbH |
| Rewoferm ® SL One | Sophorolipid | Evonik Operations GmbH |
| RHEANCE ® One | Rhamnolipid | Evonik Operations GmbH |
| Tego ® Foamex 830 | Defoamer | Evonik Operations GmbH |
| Tego ® Foamex 810 | Defoamer | Evonik Operations GmbH |
| Aerosil ® 200 | Filler | Evonik Operations GmbH |

TABLE 1.2

Pigment concentrates comprising Bayferrox 130M

| Product | CBay Amount in g | Bay1 Amount in g | Bay2 Amount in g |
|---|---|---|---|
| Water, deionized | 47.4 | 47.4 | 47.4 |
| Tego ® Dispers 755 | 30.0 | | |
| Rewoferm ® SL One | | 30.0 | |
| RHEANCE ® One | | | 30.0 |
| Tego ® Foamex 830 | 2.0 | 2.0 | 2.0 |
| Aerosil ® 200 | 0.6 | 0.6 | 0.6 |
| Bayferrox ® 130 M | 120.0 | 120.0 | 120.0 |

TABLE 1.3

Pigment concentrates comprising Heliogen Blue L7101F

| Product | CBlue Amount in g | Blue1 Amount in g | Blue2 Amount in g |
|---|---|---|---|
| Water, deionized | 42.1 | 42.1 | 42.1 |
| Tegoe ® Dispers 755 | 21.9 | | |
| Rewoferm ® SL One | | 21.9 | |
| RHEANCE ® One | | | 21.9 |
| Tego ® Foamex 810 | 1.0 | 1.0 | 1.0 |
| Heliogen Blue L7101F | 35.0 | 35.0 | 35.0 |

TABLE 1.4

Pigment concentrates comprising Special Black 4

| Product | CBlack Amount in g | Black1 Amount in g | Black2 Amount in g |
|---|---|---|---|
| Water, deionzed | 42.8 | 42.8 | 42.8 |
| Additive 1 | 31.2 | | |
| Additive 2 | | 31.2 | |
| Additive 3 | | | 31.2 |
| Tego ® Foamex 810 | 1.0 | 1.0 | 1.0 |
| Special Black 4 | 25.0 | 25.0 | 25.0 |

2. Determination of Delta E Value

For performance testing, the respective pigment concentrates from Example 1 were converted to an aqueous coating composition:

0.73 g of pigment concentrate and 19.27 g of a polyurethane-based paint of the ContiPur Satin brand from Kluthe were weighed out in a 50 ml cosmetics pot and homogenized with the aid of a Speed Mixer DAC 150 FVZ (from Hauschild) at 2000 rpm for 1 min.

Thereafter, a rub-out test was conducted in each case. The following results were obtained:

TABLE 2

|  | L* | a* | b* | Rubout ΔE |
|---|---|---|---|---|
| CBay | 66.58 | 19.30 | 6.60 | 1.08 |
| Bay1 | 67.58 | 18.73 | 6.04 | 0.61 |
| Bay2 | 67.48 | 18.04 | 4.57 | 0.85 |
| CBlue | 65.14 | −21.95 | −34.39 | 1.07 |
| Blue1 | 68.09 | −21.67 | −31.85 | 1.04 |
| Blue2 | 65.73 | −21.77 | −34.07 | 0.58 |
| CBlack | 49.05 | −0.80 | −3.35 | 1.01 |
| Black1 | 49.19 | −0.83 | −3.63 | 0.74 |
| Black2 | 49.59 | −0.81 | −3.67 | 0.68 |

On the basis of the low delta E values, the dry paint films obtained by virtue of the use according to the invention have less significant floating effects than the comparative examples. This permits the conclusion that the dried paint film has a homogeneous (colour) appearance.

TABLE 2a

Visual assessment

|  | Visual assessment |
|---|---|
| CBay | 4 |
| Bay1 | 2 |
| Bay2 | 3 |
| CBlue | 4 |
| Blue1 | 3 |
| Blue2 | 2 |
| CBlack | 4 |
| Black1 | 2 |
| Black2 | 2 |

The visual assessment shows that the dry paint films obtained through the use according to the invention have much smaller differences in hue and distinctly lower spottiness than the comparative examples.

3. Testing of Pigment Wetting Characteristics

The wetting characteristics of pigments were tested by introducing 50 g of demineralized water in each case into a 100 ml wide-neck glass bottle. Then the appropriate amount of the rhamnolipids and phospholipids according to Table 3.1 was added and the mixture was homogenized by upturning the bottle for 30 seconds to obtain a lipid-water mixture. Thereafter, 0.1 g of the pigment Heliogen Blue L7101F was applied to the surface of the lipid-water mixture, and the wetting and settling behaviour of the pigment was observed.

For the comparative example (CWetting), commercially available TEGO Dispels 755 W was used.

is The following results were obtained:

TABLE 3.1

Pigment wetting characteristics

|  | CWetting A Amount in g | Wetting1 B Amount in g | Wetting2 C Amount in g |
|---|---|---|---|
| Demineralized water | 50.0 | 50.0 | 50.0 |
| TEGO Dispers 755 W | 0.1 | | |
| Rewoferm SL ONE | | 0.1 | |
| RHEANCE ® One | | | 0.1 |
| Heliogen Blau L7101F | 0.1 | 0.1 | 0.1 |
| Time until complete wetting [min] | >>60:00 | 01:43 | 00:48 |

It was found that the pigments can be wetted more quickly on account of the use according to the invention. In the comparative example, the wetting operation took more than 60 minutes.

Figure 2:
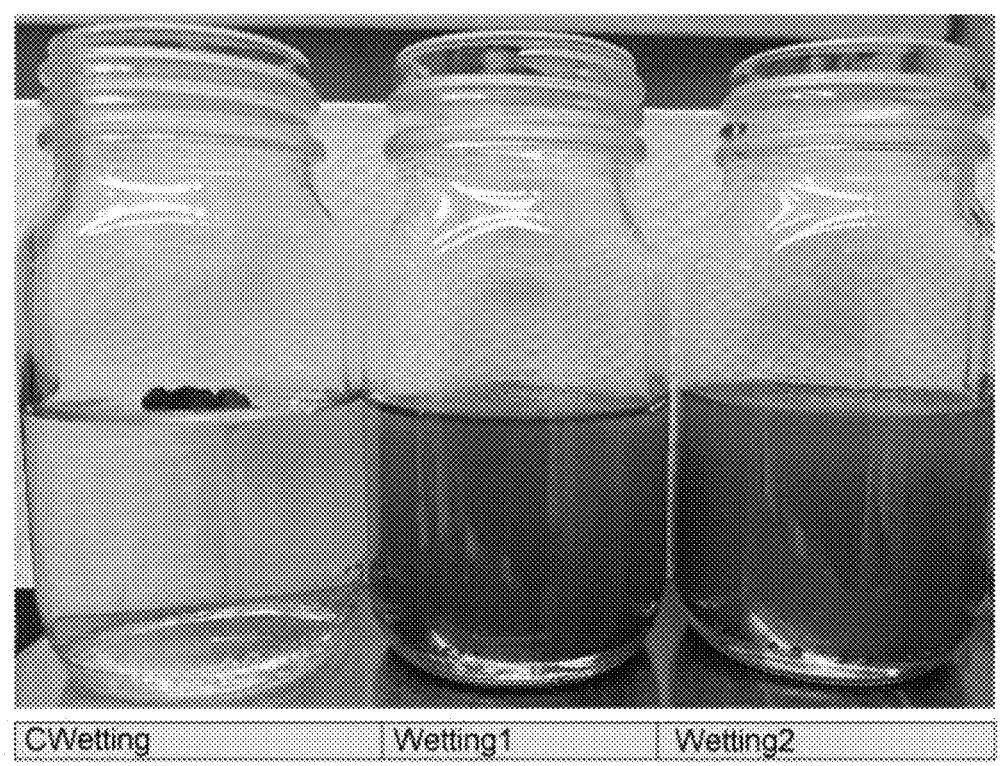
FIG. 2 shows a photograph of 3 different samples in a test of pigment wetting characteristics.

FIG. 2 shows a photograph of the 100 ml wide-neck glass bottles after 2 minutes. it is clearly apparent that the pigments are lying on the surface of the TEGO Dispers/water mixture (CWetting). Whereas, in the inventive examples, the pigments are wetted and distributed in the lipid-water mixture.

The invention claimed is:

1. A method of improving a speed of wetting pulverulent formulation constituents in a coating composition, the method comprising:
grinding with grinding bodies at least one solid selected from the group consisting of a filler, a pigment, a dye, an optical brightener, a ceramic material and a magnetic material with at least one rhamnolipid (RL) and/or at least one sophorolipid forming a ground solid in a liquid medium selected from the group consisting of an organic solvent, water and a mixture thereof.

2. The method according to claim 1, further comprising mixing said ground solid into said coating composition, wherein the coating composition is a paint or coating material selected from the group consisting of an interior wall paint, an exterior paint, an architectural paint, a floor coating, a wood paint, an industrial paint, an automotive OEM or refinishing paint, a primer, a primer-surfacer, a basecoat, and a topcoat.

3. The method according to claim 2, wherein the coating composition comprises at least one further additive.

4. The method according to claim 3, wherein the at least one further additive is selected from the group consisting of a wetting agent, a dispersing additive, a rheology additive, a levelling aid, and a defoamer.

5. The method according to claim 2, wherein the at least one rhamnolipid and/or the at least one sophorolipid is present within a range from 0.01% by weight to 10.0% by weight, based on the coating composition.

6. The method according to claim 5, wherein the at least one rhamnolipid and/or the at least one sophorolipid is present within a range from 0.1% by weight to 5.0% by weight, based on the coating composition.

7. The method according to claim 1, wherein the coating composition is formed from an additive composition that comprises the ground solid and the at least one rhamnolipid and/or the at least one sophorolipid, wherein the additive composition is a pigment concentrate, a colour paste, a pigment paste, or a millbase.

8. The method according to claim 1, wherein the at least one rhamnolipid is a compound of the general formula (I) or a salt thereof:

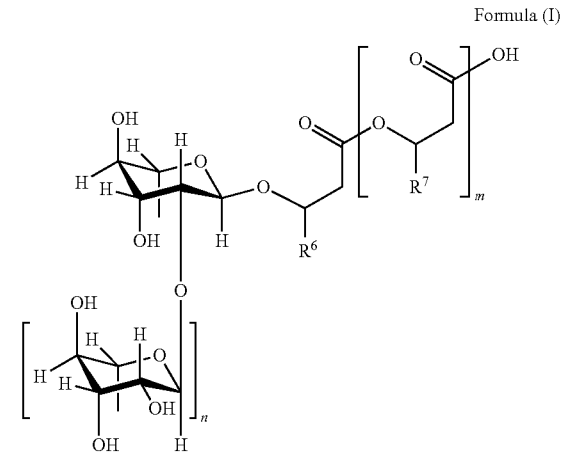

Formula (I)

wherein
m=2, 1 or 0,
n=1 or 0,
$R^6$ and $R^7$ = independently an identical or different organic radical having 2 to 24 carbon atoms.

9. The method according to claim 8, wherein in the Formula (I), $R^6$ and $R^7$ are independently an optionally branched, optionally substituted, optionally unsaturated alkyl radical having 2 to 24 carbon atoms.

10. The method according to claim 8, wherein in the Formula (I), $R^6$ and $R^7$ are independently selected from the group consisting of pentenyl, heptenyl, nonenyl, undecenyl, tridecenyl, and $(CH_2)_x$-$CH_3$ with x=1 to 23.

11. The method according to claim 1, wherein the at least one rhamnolipid is a mixed composition with >90% diRL.

12. The method according to claim 1, wherein the at least one rhamnolipid is a mixed composition comprising rhamnolipids, wherein the mixed composition contains:
51% by weight to 95% by weight of diRL-C10C10, and
0.5% by weight to 9% by weight of monoRL-C10C10,
wherein percentages by weight are based on a sum total of all rhamnolipids present, and with the proviso that a weight ratio of di-rhamnolipids to mono-rhamnolipids is greater than 91:9.

13. The method according to claim 12, wherein the weight ratio of di-rhamnolipids to mono-rhamnolipids is greater than 98:2.

14. The method according to claim 1, wherein the at least one rhamnolipid is a mixed composition comprising rhamnolipids, wherein the mixed composition contains 0.5% by weight to 15% by weight of diRL-C10C12:1, wherein percentages by weight are based on a sum total of all rhamnolipids present.

15. The method according to claim 1, wherein the at least sophorolipid is a compound of the formula (II) or (IIa):

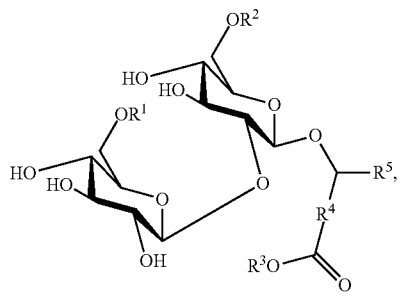

Formula (II)

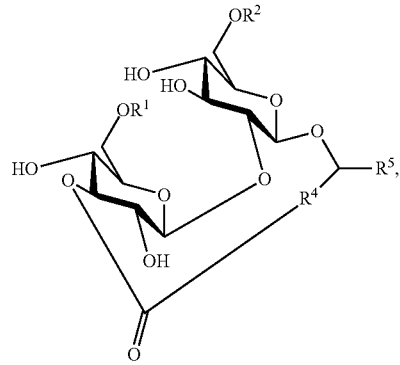

Formula (IIa)

wherein $R^1$ and $R^2$ are independently either H or an acetyl group, $R^3$ is H, a methyl, ethyl, or hexyl group, $R^4$ is independently a saturated or unsaturated divalent branched or unbranched organic group, $R^5$ is H or a methyl group, and with the proviso that a total number of carbon atoms in the groups $R^4$ and $R^5$ do not exceed 29.

16. The method according to claim 1, wherein said solid is a pigment and said ground solid has an improved homogeneous colour appearance of a dry paint film hue as compared with a coating film without rhamnolipids and/or sophorolipids.

17. The method according to claim 1 wherein an organic solvent is present which is at least one selected from the group consisting of an alkyl acetate, a hydrocarbon, an alcohol, an ether, a glycol and a glycol ether.

18. The method according to claim 1, wherein an organic solvent is present which is at least one selected from the group consisting of butyl acetate, ethyl acetate and petroleum spirits.

* * * * *